(12) United States Patent
Lögers et al.

(10) Patent No.: US 8,124,782 B2
(45) Date of Patent: Feb. 28, 2012

(54) PROCESS FOR THE PREPARATION OF 4-{4-[({[4 CHLORO-3-(TRIFLUOROMETHYL) PHENYL]AMINO}CARBONYL)AMINO] PHENOXY}-N-METHYLPYRIDINE-2-CARBOXAMIDE

(75) Inventors: Michael Lögers, Wuppertal (DE); Reinhold Gehring, Wuppertal (DE); Oliver Kuhn, Ludwigshafen (DE); Mike Matthäus, Wuppertal (DE); Klaus Mohrs, Wuppertal (DE); Matthias Müller-Gliemann, Solingen (DE); Jürgen Stiehl, Sprockhövel (DE); Mathias Berwe, Sprockhövel (DE); Jana Lenz, Wuppertal (DE); Werner Heilmann, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 952 days.

(21) Appl. No.: 11/664,332

(22) PCT Filed: Sep. 20, 2005

(86) PCT No.: PCT/EP2005/010118
§ 371 (c)(1),
(2), (4) Date: May 21, 2008

(87) PCT Pub. No.: WO2008/034796
PCT Pub. Date: Apr. 6, 2006

(65) Prior Publication Data
US 2008/0262236 A1    Oct. 23, 2008

(30) Foreign Application Priority Data
Sep. 29, 2004    (EP) .................................... 04023131

(51) Int. Cl.
*C07D 213/81*    (2006.01)
(52) U.S. Cl. ........................................................ 546/298
(58) Field of Classification Search ........................ None
See application file for complete search history.

(56) References Cited

U.S. PATENT DOCUMENTS

| | | | |
|---|---|---|---|
| 2003/0139605 A1 | 7/2003 | Riedl et al. | |
| 2003/0181442 A1 | 9/2003 | Riedl et al. | |
| 2003/0207872 A1 | 11/2003 | Riedl et al. | 514/227.8 |

FOREIGN PATENT DOCUMENTS

| | | |
|---|---|---|
| WO | WO-00 42012 | 7/2000 |
| WO | WO 03/068228 A1 * | 8/2003 |
| WO | 03047579 | 12/2003 |
| WO | 2005000284 | 6/2005 |
| WO | WO-2006 034796 | 4/2006 |

OTHER PUBLICATIONS

International Search Report, Dec. 2005.*
Motzer, et al., "Survival and Prognostic Stratification of 670 Patients With Advanced Renal Cell Carcinoma", J. Clin. Onc., 17(8): 2530-2540 (1999).
Bankston, D. et al., "A scaleable synthesis of BAY 43-9006: A potent raf kinase inhibitor for the treatment of cancer," Organic Process Research and Development, 2002, vol. 6, No. 6, pp. 777-781.
WHO Drug Information, 2003, vol. 50, No. 4, List 50.

* cited by examiner

*Primary Examiner* — Zinna Northington Davis
(74) *Attorney, Agent, or Firm* — Millen, White, Zelano & Branigan, P.C.

(57) ABSTRACT

The present invention relates to a process for preparing 4-{4-[({[4-chloro-3-(trifluoro-methyl)phenyl]amino}carbonyl) amino]phenoxy}-N-methylpyridine-2-carboxamide and its tosylate salt.

11 Claims, No Drawings

PROCESS FOR THE PREPARATION OF 4-{4-[({[4 CHLORO-3-(TRIFLUOROMETHYL) PHENYL]AMINO}CARBONYL)AMINO] PHENOXY}-N-METHYLPYRIDINE-2-CARBOXAMIDE

This application is a national stage filing of International Application PCT/EP2005/010118, filed Sep. 20, 2005.

PROCESS

The present invention relates to a process for preparing 4-{4-[({[4-chloro-3-(trifluoromethyl)-phenyl]amino}carbonyl)amino]phenoxy}-N-methylpyridine-2-carboxamide and its tosylate salt.

The tosylate salt of 4-{4-[({[4-chloro-3-(trifluoromethyl)phenyl]amino}carbonyl)amino]phenoxy}-N-methylpyridine-2-carboxamide is mentioned in WO 03/068228 and WO 03/047579 and corresponds to the compound of the formula (I):

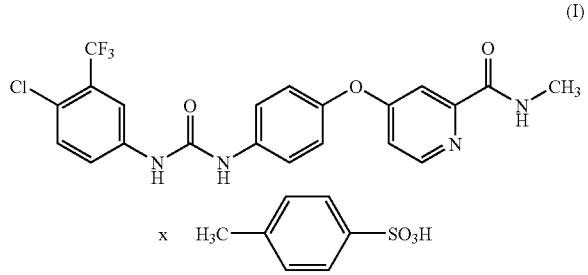

WO 03/068228 relates, inter alia, to the use of the compound of the formula (I) for treating disorders in which angiogenesis plays an important role, for example in tumor growth. WO 03/047579 relates to arylureas in combination with cytotoxic or cytostatic compounds for treating cancer.

The compound 4-{4-[({[4-Chloro-3-(trifluoromethyl)phenyl]amino}carbonyl)amino]phenoxy}-N-methylpyridine-2-carboxamide is described in WO 00/42012 and corresponds to the compound of the formula (II):

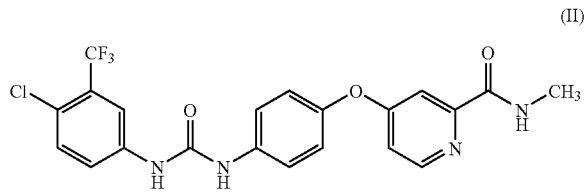

The compounds disclosed in WO 00/42012 and salts thereof, for example tosylates, are described there as inhibitors of the enzyme Raf kinase and can be used to treat disorders, for example cancer.

Both WO 00/42012 and Bankston et al. (Organic Process Research & Development, 2002, 6, 777-781) describe a process for preparing compound (II), which is illustrated in the following scheme:

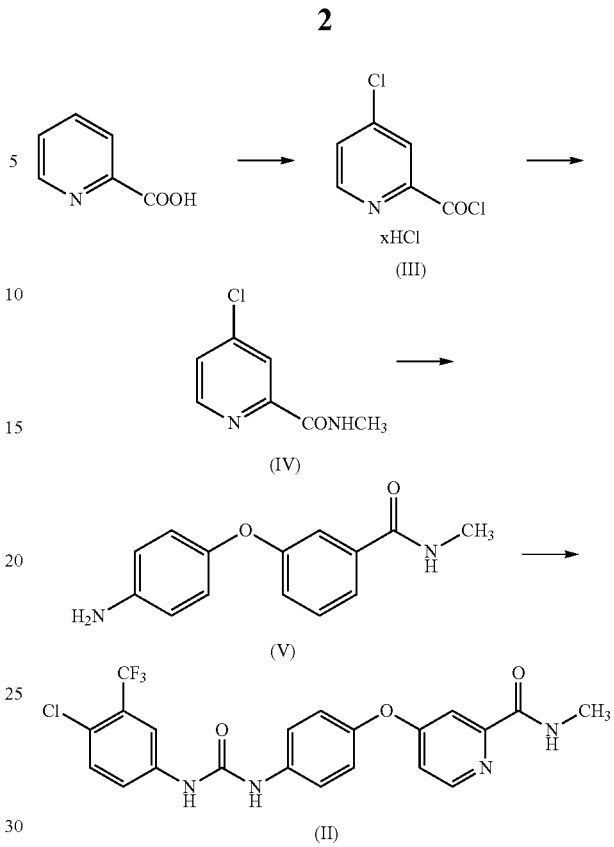

In the first step, picolinic acid is used, by reacting in thionyl chloride with addition of dimethylformamide, to prepare the acid chloride salt of the formula (III). In a second stage, this is reacted with methylamine to give the methylamide of the formula (IV), the methylamine being used dissolved in tetrahydrofuran. The subsequent reaction in dimethylformamide with 4-aminophenol with addition of potassium tert-butoxide and potassium carbonate affords the ether of the formula (V) which is isolated by extraction and converted by further reaction with 4-chloro-3-trifluoro-methylphenyl isocyanate in methylene chloride to the compound of the formula (II).

While the process disclosed by the prior art is effective for preparing the compound of the formula (II), when preparing this compound on an industrial scale, followed by the preparation of the compound of formula (I), factors such as product yields and process efficiency, safety and economy are very significant, as they are in any commercial process.

It is an object of the present invention to provide a process for preparing the compound of the formula (II) and its tosylate salt on the industrial scale (kilogram to metric tonnes range) which satisfies the criteria which apply in production and especially in the preparation of pharmaceuticals, and provides improvements in purity, environmental compatibility, industrial employability, safety aspects and volume yield. This object is achieved by the present invention.

In the inventive preparation of the compound of the formula (I) a high solubility of the compound of the formula (II) and therefore high volume yield is achieved by addition of water and/or by precharging the reaction vessel with a definite amount of p-toluenesulfonic acid. Thus, pursuant to GMP production a clarifying filtration is enabled.

In the inventive preparation of the compound of the formula (II) by reacting the compound of the formula (V) with 4-chloro-3-trifluoromethylphenyl isocyanate, it is possible, for example, to dispense with the methylene chloride solvent and to shorten the reaction time.

In the inventive preparation of the compound of the formula (V) by reacting the compound of the formula (IV) with 4-aminophenol, it is possible, compared to the prior art process, to avoid a technically costly and inconvenient extraction step, to distinctly increase the volume yield, to obtain the product with a higher purity by isolation and purification via its dihydrochloride salt and, if appropriate, to dispense with the use of dimethylformamide. Surprisingly, it is possible, compared to the prior art, also to dispense with the use of potassium carbonate.

In the inventive preparation of the compound of the formula (IV) by reacting the compound of the formula (III) with methylamine, surprisingly it is possible to use an aqueous solution in spite of the presence of the acid chloride of formula (III). In addition compared to the prior art process, for example, the workup is simplified.

In the inventive preparation of the compound of the formula (III) from 2-picolinic acid, it is possible, compared to the prior art process, to better control the course of the reaction and thus increase safety in this reaction, in particular on the industrial scale. Due to the addition of bromide compounds it is possible to dispense with the use of dimethylformamide in thionyl chloride which can form dimethylcarbamoyl chloride. It is possible likewise to dispense with an isolation of the corrosive product. The overall yield of the process according to the invention over three stages starting from 2-picolinic acid up to the compound of the formula (V) is increased compared to the prior art process.

The present invention provides a process for preparing the compound of the formula (I) which comprises, in a first step, reacting the compound of the formula (V) with 4-chloro-3-trifluoro-methylphenyl isocyanate in a nonchlorinated organic solvent, inert toward isocyanates, at a temperature above 15° C. to give the compound of the formula (II) and, in a second step, admixing the compound of the formula (II) with p-toluenesulfonic acid.

Preparation of the Compound of the Formula (I):

The present invention comprises a process for preparing the compound of the formula (I) by reacting the compound of the formula (II) with p-toluenesulfonic acid, wherein the reaction is effected in a polar solvent at a reaction temperature of from 40° C. up to the reflux temperature of the solvent used.

The inventive preparation of the compound of the formula (I) is effected by reacting the compound of the formula (II) with p-toluenesulfonic acid in a polar solvent at a reaction temperature of, for example, from 40° C. up to the reflux temperature of the solvent used, preferably at from 50° C. up to the reflux temperature of the solvent used, more preferably at from 50° C. to 90° C. In order to improve the solubility of the compound of the formula (II), if appropriate, to enable a clarifying filtration and to reduce the amount of solvent, so that the compound of the formula (II) is kept in solution, the compound of the formula (II) is first reacted with less than 1 mol, preferably with from 0.10 to 0.7 mol, more preferably with from 0.13 to 0.4 mol, of p-toluenesulfonic acid, based in each case on 1 mol of the compound of the formula (II). The preferred areas of the amount of firstly admixed p-toluenesulfonic acid can vary marginally dependent on the solvent used. If appropriate, water, preferably 12 to 14% water based on amount of organic solvent, can be admixed. Subsequently, the reaction mixture is brought to reaction temperature and is, if appropriate, filtered. Afterward, the remaining amount of the required amount of p-toluenesulfonic acid is added. Optionally, the reaction mixture is admixed with seed crystals of the compound of the formula (I) and cooled. The compound of the formula (I) is finally isolated by crystallization and filtration. If water was added to the reaction mixture, the yield of the compound of formula (I) can be increased by removing water, for example by distillation, and/or by addition of polar solvent. Thereafter the water content in the reaction mixture is equal or less than 5%. The compound of the formula (II) may, if appropriate, be used in the form of the crude product from the preceding stage or in the form of a solution or suspension, for example dissolved in ethyl acetate or tetrahydrofuran.

In the inventive preparation of the compound of the formula (I) by admixing the compound of the formula (II) with p-toluenesulfonic acid, water is added to the reaction mixture and, if appropriate, a clarifying filtration is conducted.

Particular preference is given to initially charging the compound of the formula (II) in a polar solvent and to adding the p-toluenesulfonic acid, if appropriate dissolved or suspended in a polar solvent.

p-Toluenesulfonic acid may be used either in anhydrous form or in the form of hydrates. Preference is given to using p-toluenesulfonic acid monohydrate.

The amount of p-toluenesulfonic acid required for the inventive preparation of the compound of the formula (I) is greater than or equal to 1 mol, preferably from 1 to 3 mol, more preferably from 1 to 1.5 mol, based in each case on 1 mol of the compound of the formula (II). The concentration of the compound of the formula (II) in the reaction mixture is, for example, from 5 to 30, preferably from 5 to 15, percent by weight. The concentration of p-toluenesulfonic acid in the reaction mixture is, for example, from 1 to 15, preferably from 2 to 10, percent by weight.

Suitable polar solvents in the inventive preparation of the compound of the formula (I) are, for example, organic solvents containing at least one hydroxyl group, tetrahydrofuran, ethyl acetate or mixtures of the solvents mentioned. Preferred solvents are methanol, ethanol, n-propanol, isopropanol, n-butanol, sec-butanol, isobutanol, n-pentanol, glycerol, ethylene glycol, dioxane, dimethoxyethane, tetrahydrofuran, ethyl acetate or mixtures of the solvents mentioned. Particular preference is given to ethanol, tetrahydrofuran, isopropanol, ethyl acetate or mixtures of the solvents mentioned.

In order to increase the solubility of the reaction mixture and reduce the amount of solvent and thus increase the volume yield, surprisingly it is possible to add a definite amount of water to the solvent used. This is the more surprisingly because the compound of the formula (I) and the compound of the formula (II) are both poor soluble in water alone (each <0.01 mg/100 ml at 25° C.). When water is added to the solvent, preference is given to attaining a solvent/water ratio of, for example, from 4:1 to 60:1, preferably from 6:1 to 55:1. However, the amount of water should not be so large that the crystallization of the compound of the formula (I) is prevented. Otherwise water can be removed, for example, by distillation. Preferably the water content at crystallization is equal or less then 5%.

Preparation of the Compound of the Formula (II):

The present invention additionally comprises a process for preparing the compound of the formula (II) by reacting the compound of the formula (V) with 4-chloro-3-trifluoromethylphenyl isocyanate, wherein the reaction is effected in a nonchlorinated organic solvent, inert toward isocyanates.

The inventive reaction of the compound of the formula (V) with the commercially available 4-chloro-3-trifluoromethylphenyl isocyanate to give the compound of the formula (II) is effected at a temperature above 15° C. and below 70° C., for example at a temperature of from 20° C. to 60° C., preferably at from 25° C. to 60° C., more preferably at from 30° C. to 60° C. Preference is given to initially charging the compound of the formula (V) at a temperature of from 20° C. to 60° C., more preferably at from 30° C. to 50° C., in a suitable organic solvent, and to admixing with 4-chloro-3-trifluoromethylphenyl isocyanate, if appropriate dissolved or suspended in a suitable solvent, in such a way that the reaction temperature does not exceed 70° C., preferably 65° C., more preferably 60° C. If appropriate, the crude product of the compound of the formula (II) is used in the following stage dissolved or suspended in a suitable solvent, preferably in tetrahydrofuran or ethyl acetate. The compound of the formula (II) is isolated preferably by crystallization from the reaction mixture, by cooling the reaction mixture, for example, to a temperature of from −10 to 40° C., preferably from 0 to 30° C., more preferably from 10 to 25° C.

Suitable organic solvents in the reaction of the compound of the formula (V) with 4-chloro-3-trifluoromethylphenyl isocyanate to give the compound of the formula (II) are non-chlorinated organic solvents which are inert toward isocyanates, preferably tetrahydrofuran, ethyl acetate, dioxane, methyl tert-butyl ether, dimethoxyethane or mixtures of the solvents mentioned. Particular preference is given to ethyl acetate or tetrahydrofuran.

4-Chloro-3-trifluoromethylphenyl isocyanate is used in an amount of from 0.9 to 5 mol, preferably from 1 to 3 mol, more preferably from 1 to 2 mol, based in each case on 1 mole of the compound of the formula (V). The concentration of 4-chloro-3-trifluoromethylphenyl isocyanate in the reaction mixture is from 5 to 30 percent by weight, preferably from 10 to 20 percent by weight, and the concentration of the compound of the formula (V) in the reaction mixture is from 5 to 30 percent by weight, preferably from 10 to 20 percent by weight.

It is possible to use the compound of the formula (II) in solution in the following stage without any further work-up or isolation.

Preparation of the Compound of the Formula (V):
Variant A:

The present invention likewise comprises a process for preparing the compound of the formula (V) by reacting the compound of the formula (IV) with 4-aminophenol without adding a carbonate salt.

The compound of the formula (IV) is preferably reacted with 4-aminophenol to give the compound of the formula (V) in the presence of a base in a suitable solvent at a temperature of from 25° C. up to the reflux temperature of the solvent, preferably at from 60 to 110° C., within from 1 to 12 hours, preferably within from 1 to 7 hours, more preferably within from 1 to 4 hours. For example, it is cooled to from 0 to 30° C., preferably to from 5 to 25° C. In order to achieve a higher purity, compared to the prior art, of the compound of the formula (V), the acid salt of the compound of the formula (V) is first precipitated, isolated, dissolved again, admixed with a base, and then the compound of the formula (V) is isolated by crystallization.

Particular preference is given to precipitating the acid salt of the compound of the formula (V) by admixing the reaction mixture comprising the compound of the formula (V) with tetrahydrofuran, cooling to a temperature of from −10° C. to 25° C. and adding an acid, preferably hydrochloric acid, more preferably an aqueous hydrochloric acid solution, to the reaction mixture in such a way that, if appropriate, the temperature of 50° C., preferably 40° C., more preferably 30° C., is not exceeded. Stirring is continued for up to 10 hours, preferably up to 5 hours, and the acid salt of the compound of the formula (V), preferably the dihydrochloride salt of the compound of the formula (V), is precipitated and isolated. After dissolution of the acid salt of the compound of the formula (V) in, for example, water, a pH of from 2 to 5, preferably from 2.8 to 4, is established with a base, preferably an aqueous alkali metal hydroxide solution, more preferably with an aqueous sodium hydroxide solution, and, if appropriate, admixed with seed crystals of the compound of the formula (V). Subsequently, an approximately neutral pH, preferably a pH of from 6 to 7, is established by adding a base, preferably by adding an aqueous alkali metal hydroxide solution, more preferably by adding an aqueous sodium hydroxide solution, and isolated by crystallizing the compound of the formula (V).

In order to enable satisfactory crystallization of the acid salt of the compound of the formula (V), the weight ratio, after addition of tetrahydrofuran, between solvent used and tetrahydrofuran is from 5:1 to 1:2, preferably from 3:1 to 1:2, more preferably from 2.5:1 to 1.5:1.

A suitable solvent in the inventive reaction to give the compound of the formula (V) according to variant A is a dipolar aprotic solvent. Preference is given to dimethylformamide, dimethyl sulfoxide, N-methylpyrrolidone, sulfolane or mixtures of the solvents mentioned. Particular preference is given to dimethylformamide.

Suitable bases in the inventive reaction to give the compound of the formula (V) with 4-aminophenol according to variant A are alkali metal hydroxides and alkali metal alkoxides. Preference is given to potassium tert-butoxide. Potassium tert-butoxide is preferably used in solution, more preferably in a tetrahydrofuran solution.

In the inventive reaction to give the compound of the formula (V) according to variant A, 4-aminophenol is used in an amount of from 0.9 to 5 mol, preferably from 1 to 3 mol, more preferably from 1 to 2 mol, and the base in an amount of from 1 to 3 mol, preferably from 1 to 2 mol, based in each case on 1 mole of the compound of the formula (IV). The concentration of 4-aminophenol in the reaction mixture is from 1 to 30 percent by weight, preferably from 4 to 15 percent by weight.

Variant B:

The present invention likewise comprises a process for preparing the compound of the formula (V) by reacting the compound of the formula (IV) with 4-aminophenol in the presence of water, if appropriate with addition of a phase transfer catalyst.

The reaction of the compound of the formula (IV) with 4-aminophenol to give the compound of the formula (V) according to variant B is effected in the presence of a base, in the presence of water and, if appropriate, with addition of a phase transfer catalyst, in a suitable solvent at a temperature of from 25° C. up to the reflux temperature of the solvent, preferably at from 40 to 90° C., more preferably from 50 to 80° C., within from 1 to 24 hours, preferably within from 2 to 15 hours, more preferably within from 4 to 12 hours. In order to achieve a higher purity of the compound of the formula (V) compared to the prior art, the acid salt of the compound of the formula (V) is precipitated, isolated, dissolved again, admixed with a base, and the compound of the formula (V) is isolated by crystallization.

Particular preference is given to precipitating the acid salt of the compound of the formula (V) by cooling the reaction mixture comprising the compound of the formula (V) to a temperature of from −10° C. to 25° C. and adding an acid, preferably hydrochloric acid; more preferably an aqueous hydrochloric acid solution, to the reaction mixture, in such a way that, if appropriate, the temperature of 50° C., preferably 40° C., more preferably 30° C., is not exceeded. Stirring is continued for up to 10 hours, preferably up to 5 hours, and the acid salt of the compound of the formula (V), preferably the dihydrochloride salt of the compound of the formula (V), is precipitated and isolated. After dissolution of the acid salt of the compound of the formula (V) in, for example, water, a pH of from 2 to 5, preferably from 2.8 to 4, is established with a base, preferably with an aqueous alkali metal hydroxide solution, more preferably with an aqueous sodium hydroxide solution, and the mixture is admixed, if appropriate, with seed crystals of the compound of the formula (V). Subsequently, an approximately neutral pH, preferably a pH of from 6 to 7, is established by adding base, preferably by adding an aqueous alkali metal hydroxide solution, more preferably by adding an aqueous sodium hydroxide solution and the compound of the formula (V) is isolated by crystallization.

Suitable phase transfer catalysts are tetraalkylammonium salts. Preference is given to tetraalkylammonium bromide, tetraalkylammonium chloride, tetraalkylammonium iodide, tetraalkylammonium dihydrogenphosphate or tetraalkylammonium hydrogensulfate. Particular preference is given to tetrabutylammonium hydrogensulfate.

Suitable solvents in the inventive reaction to give the compound of the formula (V) according to variant B are alkylaromatics, dimethyl sulfoxide, dimethylformamide, sulfolane, N-methyl-pyrrolidone, tetrahydrofuran or a mixture of the solvents mentioned. Suitable with preference are toluene, dimethyl sulfoxide, dimethylformamide, sulfolane, N-methylpyrrolidone, tetrahydrofuran or a mixture of the solvents mentioned. Particular preference is given to tetrahydrofuran.

Suitable bases in the inventive reaction to give the compound of the formula (V) according to variant B are alkali metal or alkaline earth metal hydroxides or alkali metal alkoxides. Preference is given to alkali metal or alkaline earth metal hydroxides. Particular preference is given to sodium hydroxide or potassium hydroxide. The base may be added without solvent and/or as an aqueous solution.

In the inventive reaction to give the compound of the formula (V) according to variant B, 4-aminophenol is used in an amount of from 0.9 to 5 mol, preferably in an amount of from 1 to 5 mol, more preferably from 1 to 3 mol, and the base in an amount of from 1 to 10 mol, preferably from 1 to 7 mol, more preferably from 2 to 5 mol, based in each case on 1 mole of the compound of the formula (IV). The concentration of 4-aminophenol in the reaction mixture is from 5 to 30 percent by weight, preferably from 5 to 15 percent by weight, and the concentration of the base in the reaction mixture is from 5 to 30 percent by weight, preferably from 5 to 15 percent by weight. The amount of water in the reaction mixture is from 1 to 30 percent by weight, preferably from 2 to 20 percent by weight, more preferably from 4 to 15 percent by weight, based on the amount of solvent used. In the presence of a phase transfer catalyst, the phase transfer catalyst is used in an amount of from 0.1 to 1 mol, preferably from 0.1 to 0.5 mol, more preferably from 0.1 to 0.3 mol, based on 1 mole of the compound of the formula (IV). The concentration of the phase transfer catalyst in the reaction mixture is from 1 to 15 percent by weight, preferably from 2 to 10 percent by weight.

When tetrahydrofuran is used as a solvent in the inventive reaction to give the compound of the formula (V) according to variant B, the weight ratio between tetrahydrofuran and water is preferably from 99:1 to 80:20, preferably from 98:2 to 90:10. The water present in the reaction solution may, for example, be added in the form of an aqueous solution of a base.

Preparation of the Compound of the Formula (IV):

The present invention likewise comprises a process for preparing the compound of the formula (IV) by reacting the compound of the formula (III) with an aqueous methylamine solution.

Instead of the aqueous methylamine solution, it is also possible to use gaseous methylamine.

In order to simplify the workup and the further reaction to give the compound of the formula (V) compared to the prior art, an aqueous methylamine solution is initially charged or gaseous methylamine is used and the formed crude product of the compound of the formula (IV) is used without isolation in the subsequent reaction to give the compound of the formula (V).

Preference is given to reacting initially charged methylamine in an aqueous solution at a temperature of from −20° C. to 30° C., preferably at from −15° C. to 20° C., more preferably at from −10° C. to 10° C., with the compound of the formula (III), dissolved or suspended in a water-immiscible organic solvent, in such a way that the reaction mixture does not exceed a temperature of 60° C., preferably of 50° C., more preferably of 40° C. If appropriate, stirring is continued at a temperature of from 10° C. to 30° C., preferably from 15 to 25° C., for up to 4 hours. After phase separation, which is, if appropriate, eased by adding sodium chloride, the compound of the formula (IV) is isolated.

In the reaction of the compound of the formula (III) with methylamine, the compound of the formula (III) is preferably used dissolved or suspended in a water-immiscible organic solvent, for example alkylaromatics or chloroaromatics, preferably xylene, toluene, trifluoromethylbenzene, methyltetrahydrofuran, methyl tert-butyl ether or chlorobenzene, dichlorobenzene, more preferably toluene. Particular preference is given to dissolving the compound of the formula (III) in toluene and adding it to an aqueous methylamine solution. The weight ratio between toluene and water in the reaction mixture is from 2:1 to 1:2.

Methylamine is used in excess, preferably in an amount of from 2 to 5 mol, based in each case on 1 mole of the compound of the formula (III). The concentration of methylamine in the reaction mixture is from 5 to 30 percent by weight, preferably from 5 to 15 percent by weight.

Preference is given to using the compound of the formula (IV) without isolation in the subsequent reaction to give the compound of the formula (V). After phase separation, particular preference is given to not isolating the crude product of the compound of the formula (IV) by fully removing the solvent, but rather using it in solution in the subsequent reaction to give the compound of the formula (V).

A purification of the compound of the formula (IV) and conversion to a storage-stable form can be effected, for example, if appropriate, by isolating the acid salt, preferably the hydrochloric acid salt of the compound of the formula (IV). To this end, a solution comprising the crude compound of the formula (IV) is admixed with an acid, preferably with hydrochloric acid, more preferably with an aqueous hydrochloric acid solution, in such a way that the reaction temperature does not exceed 60° C., preferably 50° C., more preferably 40° C. After cooling, the acid salt, preferably the hydrochloric acid salt, of the compound of the formula (IV) is isolated by crystallisation.

Preparation of the Compound of the Formula (III):

The present invention likewise comprises a process for preparing the compound of the formula (III) by reacting 2-picolinic acid with thionyl chloride, wherein a solvent inert toward thionyl chloride is used, the thionyl chloride is added to the 2-picolinic acid and the use of dimethylformamide is avoided.

In the preparation of the compound of the formula (III), 2-picolinic acid is initially charged in a solvent inert toward thionyl chloride at from 30° C. to 90° C., preferably at from 40° C. to 80° C., and reacted with thionyl chloride in such a way that gas evolution can be controlled efficiently. For example, stirring is continued at a temperature of from 40 to 110° C., preferably from 50 to 100° C., for up to 24 hours. The reaction takes place, if appropriate, in the presence of a bromide compound, preferably hydrogen bromide, lithium bromide, sodium bromide, potassium bromide, 2-picolinic acid hydrobromide or thionyl bromide, more preferably hydrogen bromide. The use of dimethylformamide is avoided. After cooling to a temperature of, for example, from 10° C. to 40° C., the volatile constituents, for example the solvent or residues of thionyl chloride, are removed preferably by applying a vacuum, and the compound of the formula (III) is isolated.

The bromide compound is added to the reaction solution at the start of the reaction or after thionyl chloride addition. Preference is given to adding sodium bromide, potassium bromide or thionyl bromide at the start of the reaction. Hydrogen bromide, for example as a gas or as an acetic acid solution, is preferably added to the reaction solution from 1 to 5 hours, preferably from 1 to 2 hours, after addition of thionyl chloride.

In the preparation of the compound of the formula (III), particular preference is given to adding hydrogen bromide, in gaseous form or as a solution. A suitable hydrogen bromide solution is a solution of hydrogen bromide in acetic acid.

A useful solvent in the preparation of the compound of the formula (III) is a solvent inert toward thionyl chloride, preferably a chlorinated aromatic hydrocarbon, or a higher-boiling, chlorinated aliphatic hydrocarbon, more preferably chlorobenzene.

Preference is given to dissolving or suspending the compound of the formula (III) without isolation in a suitable solvent, preferably in a water-immiscible, organic solvent, for example xylene, toluene, trifluoromethyl benzene, methyl tetrahydrofuran, methyl tert-butyl ether or chlorobenzene, preferably toluene, and using it in the subsequent reaction to give the compound of the formula (IV).

Thionyl chloride is used in excess, preferably in an amount of from 2 to 15 mol, preferably from 2 to 8 mol, more preferably from 2 to 6 mol, based in each case on 1 mol of 2-picolinic acid. Hydrogen bromide is used in an amount of from 0.1 to 0.5 mol, preferably from 0.1 to 0.3 mol, based in each case on 1 mole of 2-picolinic acid. Sodium bromide is used in an amount of from 0.1 to 0.5 mol, preferably from 0.1 to 0.3 mol, based in each case on 1 mole of 2-picolinic acid. Thionyl bromide is used in an amount of from 0.01 to 0.2 mol, preferably from 0.02 to 0.15 mol, based in each case on 1 mole of 2-picolinic acid. The concentration of thionyl chloride in the reaction mixture is from 30 to 80 percent by weight, preferably from 40 to 70 percent by weight, and the concentration of 2-picolinic acid in the reaction mixture is from 5 to 40 percent by weight, preferably from 10 to 25 percent by weight. The concentration of hydrogen bromide in the reaction solution is from 0.5 to 10, preferably from 0.75 to 5, percent by weight, the concentration of sodium bromide in the reaction solution is from 1 to 10, preferably from 1 to 5, percent by weight, the concentration of thionyl bromide in the reaction solution is from 0.5 to 10, preferably from 0.75 to 5, percent by weight.

The present invention comprises a process for preparing the compound of the formula (I), if appropriate starting from 2-picolinic acid by reacting with thionyl chloride to give the compound of the formula (III) as described under "Preparation of the compound of the formula (III)", if appropriate subsequently reacting the compound of the formula (III) with an aqueous methylamine solution to give the compound of the formula (IV) as described under "Preparation of the compound of the formula (IV)", if appropriate subsequently reacting the compound of the formula (IV) with 4-aminophenol to give the compound of the formula (V) as described under "Preparation of the compound of the formula (V)", subsequently reacting the compound of the formula (V) with 4-chloro-3-trifluoromethyl-phenyl isocyanate as described under "Preparation of the compound of the formula (II)" and finally reacting the compound of the formula (II) with p-toluenesulfonic acid as described under "Preparation of the compound of the formula (I)".

Preference is given to a process for preparing the compound of the formula (I), wherein, in a first step, the compound of the formula (V) is reacted with 4-chloro-3-trifluoromethyl-phenyl isocyanate in a nonchlorinated organic solvent, inert toward isocyanates, at a temperature above 15° C. to give the compound of the formula (II) and, in a second step, the compound of the formula (II) is admixed with p-toluenesulfonic acid.

Preference is likewise given to obtaining the compound of the formula (I) by first reacting the compound of the formula (IV) with 4-aminophenol without adding a carbonate salt to give the compound of the formula (V) and, if appropriate, precipitating the hydrochloric acid salt of the compound of the formula (V) in the presence of tetrahydrofuran and/or water, dissolving it in water and, by establishing a pH of from 6 to 7, isolating the compound of the formula (V) by crystallization, secondly reacting the compound of the formula (V) with 4-chloro-3-trifluoromethylphenyl isocyanate in ethyl acetate to give the compound of the formula (II), and thirdly reacting the compound of the formula (II) with p-toluenesulfonic acid.

Particular preference is given to a process for preparing the compound of the formula (I), wherein, in a first step, the compound of the formula (V) is reacted with 4-chloro-3-trifluoromethylphenyl isocyanate in a nonchlorinated organic solvent, inert toward isocyanates, at a temperature above 15° C. to give the compound of the formula (II) and, in a second step, the compound of the formula (II) is reacted with p-toluenesulfonic acid in a polar solvent at a reaction temperature of from 40° C. up to the reflux temperature of the solvent used.

Particular preference is likewise given to obtaining the compound of the formula (I) by first reacting 2-picolinic acid in a solvent inert toward thionyl chloride by adding thionyl chloride and, if appropriate, a bromide compound to give the compound of the formula (III), secondly adding the compound of the formula (III) without isolation, dissolved in toluene, to an aqueous methylamine solution to give the compound of the formula (IV), thirdly reacting the compound of the formula (IV) with 4-aminophenol in the presence of a base to give the compound of the formula (V), forming the hydrochloric acid salt of the compound of the formula (V) in the presence of tetrahydrofuran and/or water, dissolving it in water and, by establishing a pH of from 6 to 7, isolating the compound of the formula (V) by crystallization, fourthly reacting the compound of the formula (V) with 4-chloro-3-trifluoromethylphenyl isocyanate in, if appropriate, ethyl acetate to give the compound of the formula (II), and fifthly reacting the compound of the formula (II) with p-toluenesulfonic acid.

The present invention likewise comprises a process for preparing the compound of the formula (II), if appropriate starting from 2-picolinic acid by reacting with thionyl chloride to give the compound of the formula (III) as described under "Preparation of the compound of the formula (III)", if appropriate subsequently reacting the compound of the formula (III) with an aqueous methylamine solution to give the compound of the formula (IV) as described under "Preparation of the compound of the formula (IV)", if appropriate subsequently reacting the compound of the formula (IV) with 4-aminophenol to give the compound of the formula (V) as described under "Preparation of the compound of the formula (V)", and subsequently reacting the compound of the formula (V) with 4-chloro-3-trifluoromethylphenyl isocyanate as described under "Preparation of the compound of the formula (II)".

Preference is given to obtaining the compound of the formula (II) by firstly reacting the compound of the formula (IV) with 4-aminophenol without adding a carbonate salt to give the compound of the formula (V) and, if appropriate, precipitating the hydrochloric acid salt of the compound of the formula (V) in the presence of tetrahydrofuran and/or water, dissolving it in water and, by establishing a pH of from 6 to 7, isolating the compound of the formula (V) by crystallization, and secondly reacting the compound of the formula (V) with 4-chloro-3-trifluoromethylphenyl isocyanate in, if appropriate, ethyl acetate.

Particular preference is given to obtaining the compound of the formula (II) by firstly reacting 2-picolinic acid in a solvent inert toward thionyl chloride by adding thionyl chloride and, if appropriate, a bromide compound to give the compound of the formula (III), secondly adding the compound of the formula (III) without isolation, dissolved in toluene, to an aqueous methylamine solution and reacting it to give the compound of the formula (IV), thirdly reacting the compound of the formula (IV) with 4-aminophenol in the presence of a base to give the compound of the formula (V), forming the hydrochloric acid salt of the compound of the formula (V) in the presence of tetrahydrofuran and/or water, dissolving it in water and, by establishing a pH of from 6 to 7, isolating the compound of the formula (V) by crystallization, fourthly reacting the compound of the formula (V) with 4-chloro-3-trifluoromethylphenyl isocyanate in, if appropriate, ethyl acetate.

The reactions are generally carried out at atmospheric pressure. However, it is also possible to work at elevated pressure or at reduced pressure (for example in a range of from 0.5 to 5 bar).

The present invention likewise includes all combinations of the areas of preference.

The present invention will now be illustrated in detail with reference to nonlimiting preferred examples. Unless stated otherwise, all amounts relate to percentages by weight.

ABBREVIATIONS

DCI direct chemical ionization (in MS)
DMF dimethylformamide
DMSO dimethyl sulfoxide
EI electron impact ionization (in MS)
ESI electrospray ionization (in MS)
h hour(s)
min minute(s)
m.p. melting point
MS mass spectrometry
NMR nuclear resonance spectroscopy
THF tetrahydrofuran

WORKING EXAMPLES $^1$H-NMR spectra were recorded at room temperature using spectrometers from Bruker. Deuterium dimethylsulfoxide was used as solvent including tetramethylsilan as internal standard (if not otherwised mentioned).

MS spectra were recorded using spectrometers from Waters and Applied Biosystems. The relative signal intensity is stated (in percent based on the basis peak).

HPLC was performed using HP 100 from Hewlett Packard. The definite conditions are stated with the respective working examples.

Preparation of 4-{4-[({[4-chloro-3-(trifluoromethyl) phenyl]amino}carbonyl)amino]-phenoxy}-N-methylpyridine-2-carboxamide and its Tosylate Salt Stage 1:

4-Chloropyridine-2-carbonyl chloride hydrochloride

Method 1a:

2-Picolinic acid (60 kg, 487 mol) is suspended in chlorobenzene (85 kg) and heated to 70° C. Thionyl chloride (262.5 kg, 2206 mol) is added to such a degree that the gas evolution (mainly $SO_2$ and HCl) can be controlled efficiently. After stirring at 70° C. for 1 hour, gaseous hydrogen bromide (6 kg, 74 mol) is passed into the reaction vessel over 1 h. The reaction mixture is then heated to 90° C. and stirred for 13 h. After cooling to 30° C., excess thionyl chloride and the majority of the chlorobenzene are distilled off under reduced pressure (final vacuum 50 mbar at jacket temperature 75° C.). Toluene (120 kg) is added and the vacuum distillation is repeated (final vacuum 50 mbar at jacket temperature 75° C.) in order to remove thionyl chloride still remaining and the majority of the toluene. After toluene has again been added (225 kg), the crude 4-chloropyridine-2-carbonyl chloride hydrochloride is used in the next stage as the toluene solution.

Method 1b:

2-Picolinic acid (60 kg, 487 mol) is suspended in chlorobenzene (85 kg) and thionyl bromide (5.1 kg, 25 mol) is added. After heating to 72° C., thionyl chloride (200 kg, 1681 mol) is added to such a degree that the gas evolution (mainly $SO_2$ and HCl) can be controlled efficiently. The reaction mixture is subsequently heated to 90° C. and stirred for 13 h. After cooling to 20° C., excess thionyl chloride and the majority of the chlorobenzene are distilled off under reduced pressure (final vacuum 50 mbar at jacket temperature 75° C.). Toluene (120 kg) is added and the vacuum distillation is repeated (final vacuum 50 mbar at jacket temperature 75° C.), in order to remove thionyl chloride still remaining and the majority of the toluene. After toluene has been added again (225 kg), the crude 4-chloropyridine-2-carbonyl chloride hydrochloride is used in the next stage as the toluene solution.

Method 1c:

2-Picolinic acid (28.3 kg, 230 mol) and sodium bromide (3.8 kg, 37 mol) are suspended in chlorobenzene (40 kg). After heating to 50° C., thionyl chloride (94.5 kg, 794 mol) is added to such a degree that the gas evolution (mainly $SO_2$ and HCl) can be controlled efficiently. The reaction mixture is subsequently heated to 85° C. and stirred for 19 h. After cooling to 20° C., excess thionyl chloride and the majority of the chlorobenzene are distilled off under reduced pressure (final vacuum 50 mbar at jacket temperature 75° C.). Toluene (62 kg) is added and the vacuum distillation is repeated (final vacuum 50 mbar at jacket temperature 75° C.), in order to remove thionyl chloride still remaining and the majority of the toluene. After toluene has been added again (80 kg), the crude 4-chloropyridine-2-carbonyl chloride hydrochloride is used in the next stage as the toluene solution.

Stage 2:

4-chloro-N-methylpyridine-2-carboxamide

A reaction vessel is laden with methylamine as a 40% aqueous solution (117 kg, 1507 mol of methylamine). Water (97.5 kg) is added and the solution is cooled to −5° C. A solution of the crude 4-chloropyridine-2-carbonyl chloride hydrochloride (approx. 330 kg, including toluene, obtained from 60 kg of 2-picolinic acid by the process detailed in stage 1/method 1a) in toluene is added to such a degree that the temperature of the reaction mixture does not exceed 30° C. After stirring further at 20° C. for 1 h, the insoluble constituents are filtered out of the reaction mixture. After the phases have been separated, the organic phase is washed with water (90 kg). For better phase separation, 5 kg of sodium chloride are added. The majority of the toluene is distilled out of the organic phase under reduced pressure (final vacuum 40 mbar at jacket temperature 95° C.). The crude 4-chloro-N-methylpyridine-2-carboxamide is thus obtained as an orange- to dark brown-colored oil and is used in the next stage without further purification.

The crude product may be purified via the hydrochloride salt and isolated:

37% hydrochloric acid (354 g, 3.59 mol) is added with stirring to a solution of the crude 4-chloro-N-methylpyridine-2-carboxamide (500 g, 2.93 mol) in acetone (2 kg) to such a degree that the temperature of the reaction mixture does not exceed 40° C. After cooling to approx. 5° C., stirring is continued for 1 h. The product is filtered off, washed with acetone (580 g) and dried under reduced pressure (50° C., 80 mbar). In this way, 521 g (86% of theory) of 4-chloro-N-methylpyridine-2-carboxamide hydrochloride are obtained.

m.p. 166-168° C.

$^1$H NMR (DMSO-$d_6$, 500 MHz): δ=2.83 (d, J=4.8 Hz, 3H, NCH$_3$); 3.88 (br. s, HCl/H$_2$O); 7.77 (dd, J=1.9, 5.1 Hz, 1H, 5-H); 8.03 (d, J=1.6, 1H, 3-H); 8.63 (d, J=5.2 Hz, 1H, 6-H); 8.90 (br. s, 1H, NH)

MS [DCI, NH$_3$]: m/e=188 [M+NH$_4$]$^+$, 171 [M+H]$^+$ (M=free base).

Stage 3:

4-(4-Aminophenoxy)-N-methylpyridine-2-carboxamide

Method 3a:

In a reaction vessel, approx. 93 kg of crude 4-chloro-N-methylpyridine-2-carboxamide (obtained starting from 60 kg of 2-picolinic acid in the abovementioned reaction steps) are admixed with dimethylformamide (445 kg) and to the solution are added successively p-aminophenol (50.5 kg, 463 mol) and potassium tert-butoxide (273 kg, 487 mol of a 20% solution in tetrahydrofuran). The vessel contents are heated to 90° C. and stirred at this temperature for 2 h. After cooling to 15° C., tetrahydrofuran (212 kg) is added and 37% hydrochloric acid (116.5 kg, 1181 mol) is added to such a degree that the temperature of the reaction mixture does not exceed 30° C. After subsequently stirring for 1 h, the precipitated product is filtered off and washed twice with tetrahydrofuran (178 kg each time). After blow-drying, the product is dissolved in distilled water (570 kg) and a pH of from 3.3 to 3.5 is established initially at 20° C. by adding 10% sodium hydroxide solution (193 kg, 483 mol). At this pH, the solution is seeded with the title compound (0.5 kg) and subsequently stirred for 30 min. Afterward, addition of further 10% sodium hydroxide solution (118 kg, 296 mol) at 20° C. within 1 h establishes a pH of from 6 to 7 and the mixture is stirred for a further 30 min. The suspension is filtered, the solid is washed with distilled water (350 kg) and dried at approx. 60° C. under reduced pressure. 92 kg (78% of theory over three stages) of the title compound are obtained.

Method 3b:

In a reaction vessel, approx. 93 kg of crude 4-chloro-N-methylpyridine-2-carboxamide (obtained starting from 60 kg of 2-picolinic acid in the abovementioned reaction steps) are admixed successively with tetrahydrofuran (350 kg), 4-aminophenol (58.4 kg, 535 mol), tetra-N-butylammonium hydrogensulfate (33.1 kg, 97.5 mol), solid sodium hydroxide (29.1 kg, 726 mol) and 45% sodium hydroxide solution (65.3 kg, 734 mol). The mixture is heated to 65° C. and stirred at this temperature for 8 h. After cooling to 20° C., 37% hydrochloric acid (238 kg, 2408 mol) is added to such a degree that the temperature of the reaction mixture does not exceed 25° C. After stirring further for 1 h, the precipitated product is filtered off and washed with tetrahydrofuran (300 kg). After the still-moist product has been dissolved in water (920 kg), the pH of the mixture is adjusted to from pH 3 to 3.5 at 20° C. by adding 22.5% sodium hydroxide solution (70.7 kg, 398 mol). The mixture is seeded with the title compound (0.5 kg), and the addition of 22.5% sodium hydroxide solution (50 kg, 281 mol) is continued until a pH of from 6 to 7 has been attained. The suspension is stirred further for 1 h, and the product is subsequently filtered off, washed with water (150 kg) and dried under reduced pressure (50° C., final vacuum <40 mbar). In this way, 88 kg (74% of theory over three stages) of the title compound are obtained as light brown crystals.

m.p. 114-116° C.

$^1$H-NMR (DMSO-$d_6$, 500 MHz): δ=2.78 (d, J=4.7 Hz, 3H, NCH$_3$); 5.21 (br. s, 2H, NH$_2$); 6.64, 6.86 (AA'BB' quartett, J=8.6 Hz, 4H, aromatic); 7.08 (dd, J=2.4, 5.4 Hz, 1H, 5-H); 7.33 (d, J=2.3 Hz, 1H, 3-H); 8.46 (d, J=5.5 Hz, 1H, 6-H); 8.78 (br. d, J=4.5 Hz, 1H, NH)

MS (EI): m/e=243 [M]$^+$, 186 [M-CONHCH$_3$]$^+$, 109.

HPLC: Inertsil ODS 3, 5 μm, ID 3 mm, length 25 cm, (stationary phase); flow: 0.5 mL/min.; 245 nm; eluent A: neutral ammonium acetate buffer, eluent B: 20 mL neutral ammonium acetate buffer, 400 mL acetonitril, 400 mL methanol; linear gradient 12.5% B→100% B (15 min.).

Retention time: 12.6 min.; purity: >95%.

Stage 4:

4-{4-[({[4-Chloro-3-(trifluoromethyl)phenyl]amino}carbonyl)amino]phenoxy}-N-methylpyridine-2-carboxamide 4-(4-Aminophenoxy)-N-methyl-2-pyridinecarboxamide (52.3 kg, 215 mol) is suspended in ethyl acetate (146 kg) and the suspension is heated to approx. 40° C. 4-Chloro-3-trifluoromethylphenyl isocyanate (50 kg, 226 mol), dissolved in ethyl acetate (58 kg), is then added to such a degree that the temperature is kept below 60° C. After cooling to 20° C. within 1 h, the mixture is stirred for a further 30 min and the product is filtered off. After washing with ethyl acetate (30 kg), the product is dried under reduced pressure (50° C., 80 mbar). 93 kg (93% of theory) of the title compound are obtained as colorless to slightly brownish crystals.

m.p. 206-208° C.

$^1$H-NMR (DMSO-$d_6$, 500 MHz): δ=2.79 (d, J=4.4 Hz, 3H, NCH$_3$); 7.16 (dd, J=2.5, 5.6 Hz, 1H, 5-H); 7.18 (d, J=8.8 Hz, 2H, 3'-H, 5'-H); 7.38 (d, J=2.4 Hz, 1H, 3-H); 7.60-7.68 (m, 4H, 2'-H, 6'-H, 5"-H, 6"-H); 8.13 (d, J=1.9 Hz, 1H, 2"-H); 8.51 (d, J=5.6 Hz, 1H, 6-H); 8.81 (d, J=4.5 Hz, 1H, NHCH$_3$); 9.05 (br. s, 1H, NHCO); 9.25 (br. s, 1H, NHCO)

MS (ESI, CH$_3$CN/H$_2$O): m/e=465 [M+H]$^+$.

Stage 5:

4-{4-[({[4-Chloro-3-(trifluoromethyl)phenyl]amino}carbonyl)amino]phenoxy}-N-methylpyridine-2-carboxamide tosylate Method 5a:

4-{4-[({[4-Chloro-3-(trifluoromethyl)phenyl]amino}carbonyl)amino]phenoxy}-N-methylpyridine-2-carboxamide (47.5 kg, 100 mol) is suspended in ethanol (432 kg) and p-toluenesulfonic acid monohydrate (6.8 kg, 36 mol) is added. The mixture is stirred for 15 min. and the suspension has been heated to 74° C. within 0.5 h. After the mixture is clarified by filtration, further p-toluenesulfonic acid monohydrate (16.8 kg, 88 mol) is added within 40 min. as a filtered solution in ethanol (41 kg). The crystallization of the product is induced by seeding at 74° C. with 0.63 kg of the title compound. After cooling to 3° C. within 120 min., the mixture is stirred for a further 1 h and the product is filtered off. The solid is washed twice with ethanol (88 kg each time) and dried under reduced pressure. 58 kg (91% of theory) of the title compound are obtained as colorless to slightly brownish crystals.

m.p. 223-231° C. (melting under decomposition)

$^1$H-NMR (DMSO-$d_6$, 500 MHz): δ=2.29 (s, 3H, CH$_3$); 2.79 (d, J=4.8 Hz, 3H, NCH$_3$); 5.9 (br. s, 1H, SO$_3$H), 7.14 (d, J=7.9 Hz, 2H, 2'''-H, 6'''-H); 7.17-7.22 (m, d, J=8.8 Hz, 3H, 5-H, 3'-H, 5'-H); 7.44 (d, J=2.0 Hz, 1H, 3-H); 7.48 (d, J=8.0 Hz, 2H, 3'''-H, 5'''-H), 7.61 (d, J=8.8 Hz, 2H, 2'-H, 6'-H), 7.63 (m, 1H, 5''-H), 7.67 (m, 1H, 6''-H), 8.14 (d, J=2.2 Hz, 1H, 2''-H), 8.53 (d, J=5.6 Hz, 1H, 6-H); 8.88 (d, J=4.8 Hz, 1H, NHCH$_3$); 9.10 (br. s, 1H, NHCO); 9.30 (br. s, 1H, NHCO).

MS (ESI, CH$_3$CN/H$_2$O): m/e=465 [M+H]$^+$.

HPLC: Zorbax Eclipse XDB C-8, 3.5 μm, ID 2.1 mm, length 15 cm (stationary phase); flow: 0.6 mL/min.; 235 nm; eluent A: acidic phosphate buffer, eluent B: ethanol/acetonitril=4/6 (V/V), linear gradient 5% B->43.5% B (22 min.), subsequently linear gradient 43.5% B->90% B (8 min.).

Retention times: p-toluenesulfonic acid: (R$_t$ 1.8 min.); title compound: (R$_t$ 25.5 min.) purity: >99%.

Method 5b:

4-{4-[({[4-Chloro-3-(trifluoromethyl)phenyl]amino}carbonyl)amino]phenoxy}-N-methylpyridine-2-carboxamide (50 g, 0.1076 mol) are suspended in isopropanol (300 g). Subsequently, p-toluenesulfonic acid monohydrate (7.4 g, 0.039 mol) and 50 g of water are added. After the suspension has been heated to 74° C. within 1 h, it is filtered and a filtered solution of p-toluenesulfonic acid monohydrate (17.13 g, 0.09 mol) in isopropanol (50 g) is added at 70° C. within 40 min. After seeding at 74° C. with the title compound the mixture is cooled to 30° C. within 90 min. and isopropanol and water are distilled off under reduced pressure (70-100 mbar) within 1.5 to 3 h. During distillation isopropanol (400 g) is added. Afterward the mixture is stirred at 20° C. for 0.5 h. The product is filtered off, washed twice with isopropanol (140 g each time) and dried under reduced pressure. 61.9 g (90% of theory) of the title compound are obtained as colorless to slightly brownish crystals.

Method 5c:

4-{4-[({[4-Chloro-3-(trifluoromethyl)phenyl]amino}carbonyl)amino]phenoxy}-N-methylpyridine-2-carboxamide (50 g, 0.1076 mol) are suspended in ethyl acetate (500 g) and water (10 g). The mixture is heated to 69° C. within 0.5 h and a filtered solution of p-toluenesulfonic acid monohydrate (3.26 g, 0.017 mol) in mixture of water (0.65 g) and ethyl acetate (7.2 g) is added. After filtration a filtered solution of p-toluenesulfonic acid monohydrate (22 g, 0.11 mol) in a mixture of ethyl acetate (48 g) and water (4.34 g) is added. The mixture is cooled to 23° C. within 2 h. The product is filtered off, washed twice with ethyl acetate (92.5 g each time) and dried under reduced pressure. 65.5 g (96% of theory) of the title compound are obtained as colorless to slightly brownish crystals.

Method 5d: (Stage 4+5 as a One-Stage Process)

4-(4-Aminophenoxy)-N-methyl-2-pyridinecarboxamide (26.2 g, 0.1077 mol) is suspended in ethyl acetate (320 g) and the suspension is heated to approx. 40° C. After filtration a filtered solution of 4-chloro-3-trifluoromethylphenyl isocyanate (25 g, 0.113 mol) in ethyl acetate (32 g), is added to such a degree that the temperature is kept below 40° C. The mixture is heated to 71° C. within 30 min. and, after addition of 10 g of water, a filtered solution of p-toluenesulfonic acid monohydrate (24.8 g, 0.13 mol), in a mixture of ethyl acetate (20.4 g) and water (6.7 g), is metered in within 40 min. After filtration, seeding with the title compound at 71° C. and cooling to 25° C. within 2 h, the product is filtered off. After washing twice with ethyl acetate (92.5 g), the product is dried under reduced pressure (50° C., 125 mbar). 65.8 kg (96.0% of theory) of the title compound are obtained as colorless to slightly brownish crystals.

Method 5e: (Stage 4+5 as a One-Stage Process)

4-(4-Aminophenoxy)-N-methyl-2-pyridinecarboxamide (10.4 g, 0.0427 mol) is dissolved at 25° C. in tetrahydrofuran (44.4 g) and 4-chloro-3-trifluoromethylphenyl isocyanate (10 g, 0.0448 mol), dissolved in tetrahydrofuran (6.8 g), is added to such a degree that the temperature is kept below 25° C. The mixture is heated to 64° C. within 0.5 h and after filtration a filtered solution of p-toluenesulfonic acid monohydrate (9.7 g, 0.05 mol), dissolved in tetrahydrofuran (27 g), is added. Subsequently, the mixture is filtered, seeded with the title compound at 64° C. and cooled to 0° C. within 3 h and the product is filtered off. After washing twice with tetrahydrofuran (18.5 g), the product is dried under reduced pressure (50° C., 300 mbar). 22.2 kg (81.6% of theory) of the title compound are obtained as colorless to slightly brownish crystals.

What is claimed is:

1. A process for preparing the compound of the formula (I)

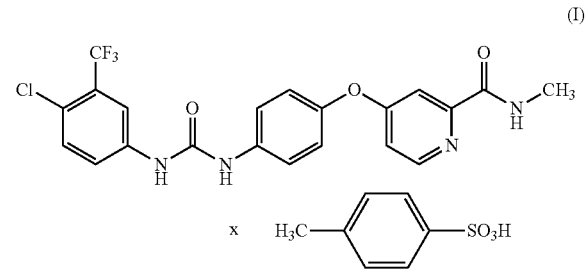

which comprises, in a first step, reacting the compound of the formula (V)

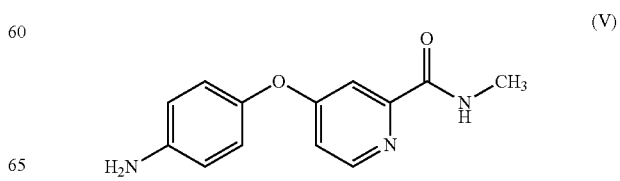

with 4-chloro-3-trifluoromethylphenyl isocyanate in a nonchlorinated organic solvent, inert toward isocyanates, by initially charging the compound of the formula (V) at a temperature of from 20° C. to 60° C. and admixing with 4-chloro-3-trifluoromethylphenyl isocyanate in such a way that the reaction temperature does not exceed 70° C. to give the compound of the formula (II)

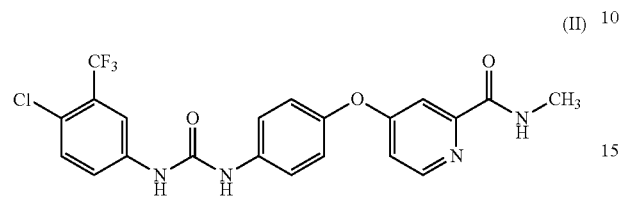

and, in a second step, admixing the compound of the formula (II) with p-toluenesulfonic acid in a polar solvent at a reaction temperature of from 40° C. up to the reflux temperature of the solvent used.

2. A process for preparing the compound of the formula (II),

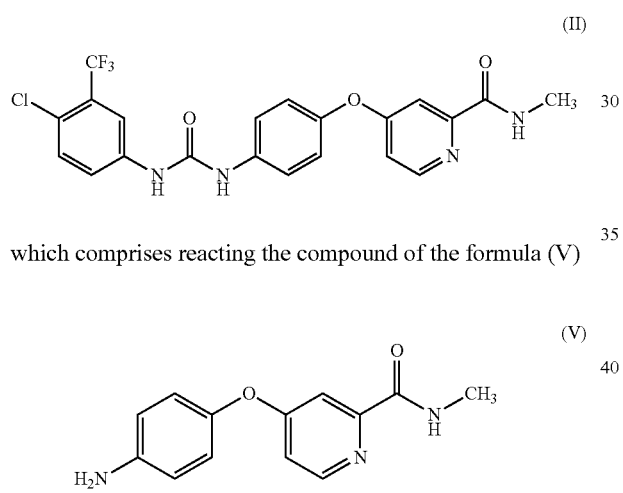

which comprises reacting the compound of the formula (V)

with 4-chloro-3-trifluoromethylphenyl in a nonchlorinated organic solvent, inert toward isocyanates, by initially charging the compound of the formula (V) at a temperature of from 20° C. to 60° C. and admixing with 4-chloro-3-trifluoromethylphenyl isocyanate in such a way that the reaction temperature does not exceed 70° C. isocyanate to give the compound of the formula (II).

3. The process of claim 1 or 2, wherein the compound of the formula (V) is prepared by reacting the compound of the formula (IV)

with 4-aminophenol without adding a carbonate salt.

4. The process of claim 1 or 2, wherein, in the preparation of the compound of the formula (V), the acid salt of the compound of the formula (V) is first precipitated, isolated, dissolved again, admixed with a base, and then the compound of the formula (V) is isolated by crystallization.

5. The process of claim 3, wherein the compound of the formula (IV) is prepared by reacting the compound of the formula (III)

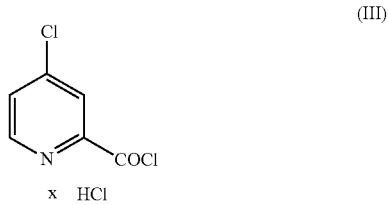

with an aqueous methylamine solution.

6. The process of claim 5, wherein the compound of the formula (III) is prepared by using a solvent inert toward thionyl chloride, adding thionyl chloride to 2-picolinic acid and without using of dimethylformamide.

7. A process for preparing the compound of the formula (I)

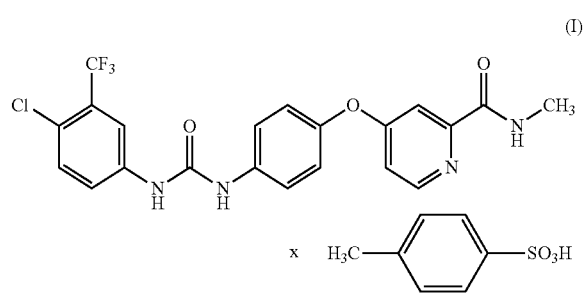

by reacting the compound of the formula (II)

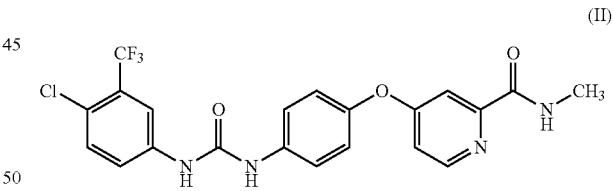

with p-toluenesulfonic acid, which comprises effecting the reaction in a polar solvent at a reaction temperature of from 40° C. up to the reflux temperature of the solvent used and admixing of water to the mixture.

8. A process for preparing the compound of the formula (I)

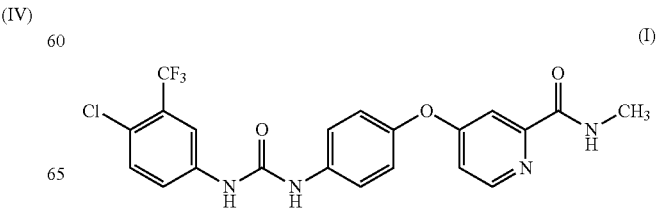

-continued x 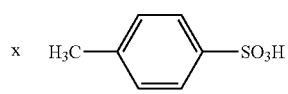

by a) reacting the compound of the formula (IV)

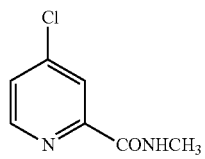

(IV)

with 4-aminophenol without adding a carbonate salt to give the compound of the formula (V)

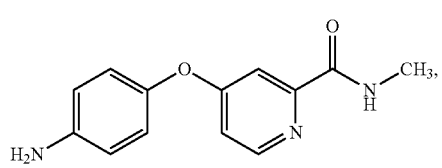

(V)

b) reacting the compound of the formula (V) with 4-chloro-3-trifluoromethylphenyl isocyanate to give the compound of the formula (II)

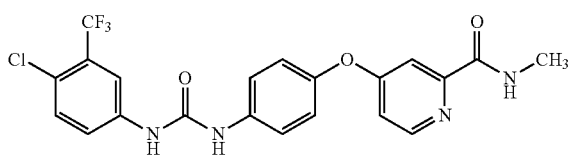

(II)

and and c) reacting the compound of the formula (II) with p-toluenesulfonic acid.

9. A process for preparing the compound of the formula (I)

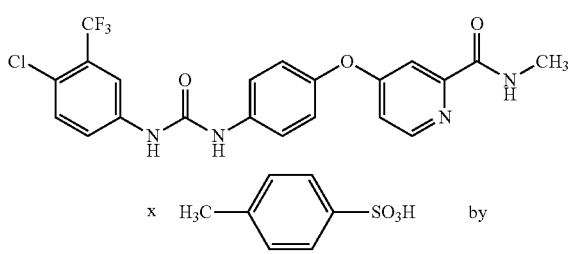

(I)

by a) reacting the compound of the formula (III)

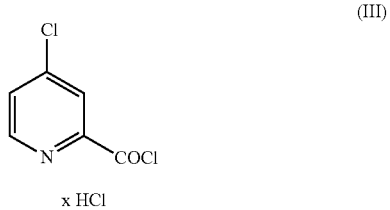

(III)

with an aqueous methylamine solution to give the compound of the formula (IV)

(IV)

b) reacting the compound of the formula (IV) with 4-aminophenol to give the compound of the formula (V),

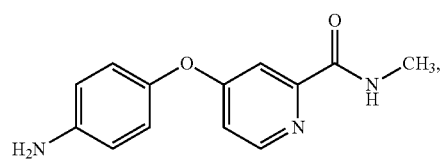

(V)

c) reacting the compound of the formula (V) with 4-chloro-3-trifluoromethylphenyl isocyanate to give the compound of the formula (II)

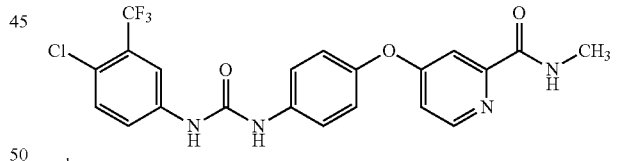

(I)

and d) reacting the compound of the formula (II) with p-toluenesulfonic acid.

10. A process for preparing the compound of the formula (I)

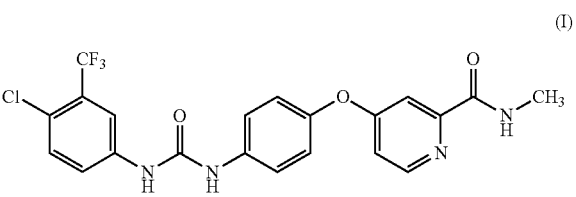

(I)

x 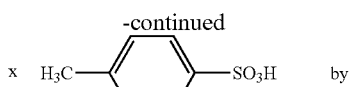 by a) adding thionyl chloride to 2-picolinic acid in a solvent inert toward thionyl chloride without using dimethylformamide and reacting to give the compound of the formula (III)

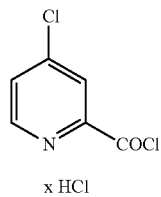

x HCl (III)

b) reacting the compound of the formula (III) with methylamine to give the compound of the formula (IV)

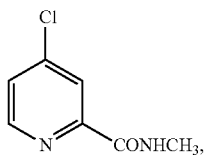

(IV)

c) reacting the compound of the formula (IV) with 4-aminophenol to give the compound of the formula (V)

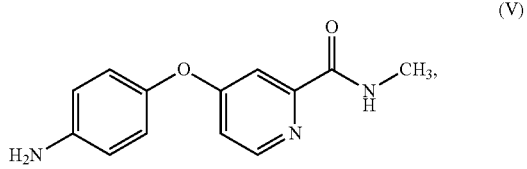

(V)

d) reacting the compound of the formula (V) with 4-chloro-3-trifluoromethyl-phenyl isocyanate to give the compound of the formula (II)

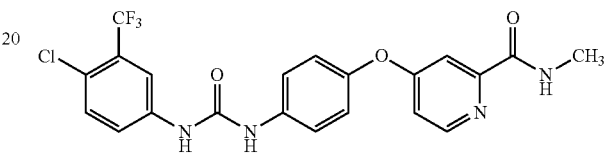

(II)

and e) reacting the compound of the formula (II) with p-toluenesulfonic acid.

11. The process of claim 1, wherein p-toluenesulfonic acid monohydrate is used.

* * * * *